United States Patent
Willeford

(10) Patent No.: US 8,972,019 B2
(45) Date of Patent: Mar. 3, 2015

(54) METHOD AND DEVICE FOR TREATING OSTEOARTHRITIS NONINVASIVELY

(76) Inventor: Kenneth L. Willeford, Little River, SC (US)

( * ) Notice: Subject to any disclaimer, the term of this patent is extended or adjusted under 35 U.S.C. 154(b) by 77 days.

(21) Appl. No.: 13/013,543

(22) Filed: Jan. 25, 2011

(65) Prior Publication Data

US 2012/0191159 A1  Jul. 26, 2012

(51) Int. Cl.
| | | |
|---|---|---|
| *A61N 1/39* | (2006.01) | |
| *A61H 1/00* | (2006.01) | |
| *A61H 1/02* | (2006.01) | |
| *A61H 5/00* | (2006.01) | |
| *A61N 1/32* | (2006.01) | |
| *A61N 7/00* | (2006.01) | |
| *A61F 2/28* | (2006.01) | |

(52) U.S. Cl.
CPC ...... *A61N 1/326* (2013.01); *A61N 7/00* (2013.01); *A61F 2/28* (2013.01); *A61F 2002/2821* (2013.01); *A61N 2007/0013* (2013.01)
USPC ................................................ 607/51; 601/2

(58) Field of Classification Search
CPC . A61N 7/00; A61N 1/326; A61N 2007/0078; A61F 2/28
USPC ............ 607/2, 46, 108, 58, 50–51; 601/2
See application file for complete search history.

(56) References Cited

U.S. PATENT DOCUMENTS

| | | | |
|---|---|---|---|
| 4,530,360 A | 7/1985 | Duarte | |
| 4,818,697 A | 4/1989 | Liboff et al. | |
| 4,932,951 A | 6/1990 | Liboff et al. | |
| 5,059,298 A | 10/1991 | Liboff | |
| 5,139,474 A | 8/1992 | Lamond et al. | |
| 5,195,940 A | 3/1993 | Baylink | |
| 5,330,410 A | 7/1994 | Baylink | |
| 5,413,550 A * | 5/1995 | Castel ............................. 601/2 |
| 5,520,612 A * | 5/1996 | Winder et al. ................... 601/2 |
| 5,752,924 A | 5/1998 | Kaufman et al. | |
| 5,972,040 A | 10/1999 | Moss et al. | |
| 6,652,473 B2 | 11/2003 | Kaufman et al. | |
| 6,955,642 B1 | 10/2005 | Simon | |
| 7,354,748 B2 | 4/2008 | Brighton | |
| 7,468,264 B2 | 12/2008 | Brighton et al. | |
| 7,783,348 B2 | 8/2010 | Gill et al. | |
| 7,840,272 B2 * | 11/2010 | Kronberg et al. .............. 607/51 |
| 2001/0027278 A1 | 10/2001 | Kaufman et al. | |

(Continued)

OTHER PUBLICATIONS

Malizos et al., Low-intensity pulsed ultrasound for bone healing: An overview; Inury, Int. J. Care Injured (2006), pp. S56-S62.*

(Continued)

*Primary Examiner* — Catherine Voorhees
(74) *Attorney, Agent, or Firm* — Novak Druce Connolly Bove + Quigg LLP

(57) ABSTRACT

Methods and devices are provided for OA treatment of an affected area or joint. In one embodiment, the method may involve identifying a treatment site of the joint, and providing at least one transducer module at the treatment site. The at least one transducer module may be in operative communication with a signal generator module, and may include transducer(s) for delivering stimulative signals (e.g., electromagnetic signals and/or ultrasound signals). The method may also involve stimulating (a) bone remodeling, (b) bone cells and associated precursors, and/or (c) pericytes with the stimulative signals delivered to the treatment site.

16 Claims, 6 Drawing Sheets

(56) References Cited

U.S. PATENT DOCUMENTS

| | | | |
|---|---|---|---|
| 2003/0153849 A1* | 8/2003 | Huckle et al. | 601/2 |
| 2005/0197522 A1* | 9/2005 | Pilla | 600/13 |
| 2006/0116721 A1 | 6/2006 | Yun et al. | |
| 2008/0288035 A1* | 11/2008 | Gill et al. | 607/108 |
| 2009/0005710 A1* | 1/2009 | Min et al. | 601/2 |
| 2009/0062885 A1 | 3/2009 | Brighton et al. | |
| 2011/0144410 A1* | 6/2011 | Kennedy | 600/2 |
| 2012/0191018 A1* | 7/2012 | Willeford | 601/2 |

OTHER PUBLICATIONS

International Search Report and Written Opinion issued in PCT/US11/20170 mailed Apr. 30, 2012.
Oddis et al., *The American Journal of Medicine* 1996, 100(2A):10S-15S.
Felson, *Radiologic Clinics of North America* 2004, 42:1-9.
Clarke, *Clinical Journal of American Society of Nephrology* 2008, 3:S131-S139.
Hauge et al. *Journal of Bone and Mineral Research* 2001 16(9): 1575-1582.
Parfitt, *Journal of Bone and Mineral Research* 2001, 16(9): 1583-1585.
Parfitt, *Bone* 2000, 26(4): 319-323.
Felson et al., *Annals of Internal Medicine* 2003, 139 (5): 330-336.
Zanetti et al., *Radiology* 2000, 215:835-840.
Martig et al., *Veterinary Radiology Ultrasound* 2007, 48(2): 105-112.
Bergman et al. *Skeletal Radiology* 1994, 23:445-448.
Guzman et al. *Toxicologic Pathology* 2003, 31:619-624.
Felson et al., *Arthritis & Rheumatism* 2004, 50(2): 341-344.
Imhof et al., *Topics in Magnetic Resonance Imaging* 1999, 10(3):180-192.
Imhof et al., *Investigational Radiology* 2000, 35(10):581-588.
Radin et al., *Journal of Orthopaedic Research* 1884, 2(3):221-234.
Garnero et al, *Arthritis and Rheumatism* 2005, 52(9): 2822-2829.
Helal, *Postgraduate Medical Journal* 1965, 41(474):172-181.
He et al., *Acta Orthopaedics Scandanavia* 1990, 61(3):195-200.
Kofoed, *Acta Orthopaedics Scandanavia* 1986, 57:119-122.
Lemperg et al., *Clinical Orthopaedics and Related Research* 1978, 136:143-156.
Arnoldi, *The Journal of Bone and Joint Surgery* 1972, 54B(3):409-421.
Dey et al., *Annals of the Rheumatic Diseases* 1989, 48:188-193.
Cheras et al., *Clinical Orthopaedics and Related Research* 1997, 334:57-67.
Wang et al., *Journal of Biomechanics* 2003, 36: 1439-1451.
Behets et al., *Journal of Bone and Mineral Research* 2004, 19(11): 1821-1826.
Goldstein et al., *Orthopaedic Trauma* 2010, 24(3):S62-S65.
Kooistra et al., *Indian Journal of Orthopaedics* 2009, 43(2): 149-155.
Aaron et al., *Clinical Orthopaedics* 2004, 419:21-29.
Brighton et al., *Clinical Orthopaedics and Related Research* 1992, 285:255-262.
Shankar et al., *Journal of Cellular Physiology* 1998, 176: 537-544.
Brighton et al., *Journal of Orthopaedic Research* 1985, 3(3): 331-340.
Trock et al., *The Journal of Rheumatology* 1993, 20: 456-460.
Brighton et al, *Journal of Orthopaedic Research* 1983, 1(1):42-49.
Brighton et al., *Journal of Orthopaedic Research* 1989, 7(5):759-765.
Claes et al., *Progress in Biophysics and Molecular Biology*, 2007, 93(1-3):384-98.
Eriksen, *Endocrinology Review* 1986, 7:379-408.
Wiesmann et al, *Biochimica et Biophysica Acta* 2001, 1538: 28-37.
Norton, *Annals New York Academy of Sciences* 1974, p. 466-477.
Stalnecker et al, *Plastic and Reconstructive Surgery* 1988, 82(4): 580-586).
Trock et al., *The Journal of Rheumatology* 1994, 21: 1903-1911.
Baker et al., *Annals New York Academy of Sciences* 1974, p. 491-498.
Baker et al., *Clinical Orthopaedics and Related Research* 1974, 102:251-267.
Brighton et al., *The Journal of Bone and Joint Surgery* 1976, 58A(7): 971-978.
Armstrong et al., *Journal of Orthopaedic Research* 1988, 6(2): 265-271.
Langenskiold et al, *Acta Orthopaedics Scandanavia* 1979, 50:1-14.
Videman, *Acta Orthopaedics Scandanavia* 1982, 53:339-347.
Burr et al., *Clinical Orthopaedics and Related Research* 1984, 189:264-278.
Sharrard et al., *The Journal of Bone and Joint Surgery* 1982, 64B(2): 189-193.
Brighton et al., *Journal of Orthopaedic Research*, 1984, 2(1): 15-22.
Findlay D., "Vascular pathology and osteoarthritis." Rheumatology 2007, 46(12):1763-1768.
Zizac T., Hoffman K., Holt P., Hungerford D., O'Dell J., Jacobs M., Lewis C., Deal C., Caldwell J., Cholewczynski J., Free S. "The treatment of osteoarthritis of the knee with pulsed electrical stimulation." *Journal of Rheumatology* 1995, 22: 1757-1761.
Office Action dated Jun. 3, 2013 in U.S. Appl. No. 13/044,991.
International Preliminary Report on Patentability and Written Opinion of the International Searching Authority dated Jul. 30, 2013.

* cited by examiner

METHOD AND DEVICE FOR TREATING OSTEOARTHRITIS NONINVASIVELY

BACKGROUND

1. Field

Aspects of the present disclosure relate generally to a method and system for treating osteoarthritis with electromagnetic stimulation and/or ultrasound.

2. Background

Osteoarthritis (OA) of the knee is the most common form of OA affecting more than ten million Americans and is the most common cause of disability in the United States. Symptoms may include pain, stiffness, limited range of motion and localized swelling. Currently, there is no known cure for OA and current treatments are intended to mitigate the symptoms.

As shown in FIG. 1, the human knee is a synovial joint between the femur and tibia. The joint is contained within a fibrous joint capsule with a synovial membrane lining. The ends of the bones are covered with articular cartilage and the bone beneath the cartilage is the subchondral bone. Hyaline articular cartilage loss is the central signature event in OA. While the exact etiology of OA is unknown, the pathophysiology involves a combination of mechanical, cellular, and biochemical processes.

With reference to FIG. 2, there are three primary types of bone: woven bone, cortical bone, and cancellous bone. Woven bone is found during fracture healing (callus formation). Cortical bone, also called compact or lamellar bone, is remodeled from woven bone and forms the internal and external tables of flat bones and the external surfaces of long bones. Cancellous bone (trabecular bone) lies between cortical bone surfaces and consists of a network of honeycombed interstices containing hematopoietic elements and bony trabeculae. The trabeculae are predominantly oriented perpendicular to external forces to provide structural support.

Bone remodeling is the process by which bone is renewed to maintain bone strength and mineral homeostasis. Remodeling involves continuous removal of discrete packets of old bone, replacement of these packets with newly synthesized proteinaceous matrix, and subsequent mineralization of the matrix to form new bone. The remodeling process resorbs old bone and forms new bone and cancellous bone is continually undergoing remodeling on the internal endosteal surfaces.

There is a vascular component which is integrally associated with the process of bone remodeling. This vascular contribution has both an anatomic basis and functional relevance. The subchondral region is highly vascular with terminal vessels in direct contact with the deepest hyaline cartilage layer. Bone remodeling occurring in a bone chamber is also related to the existence of and increased flow through microvessels that conform closely to the contour of the cancellous bone surface. Pericytes are intimately involved in the process of angiogenesis which accompanies the vascular component involved with cancellous bone remodeling. The microvasculature has been linked to the regulation of coupling between bone resorption and bone formation. This structure forms the anatomic basis for the knowledge that the vascular system is associated with osteogenesis during bone remodeling.

Cellular changes have been identified in osteoarthritis of the knee to include bone marrow edema, extensive intertrabecular fibrosis and sclerosis, as well as vascularization and thickening of the trabeculae in the subchondral bone. These combine to increase the stiffness of the subchondral bone, transmitting increased load to the overlying cartilage and leading to secondary cartilage damage. The increased venous vascular resistance contributes to venous congestion, increased intraosseous pressure, congestive bone pain, diminished nutrient delivery and progression of the disease. There is an interrelationship between cartilage damage and subchondral bone integrity.

The current understanding of the pathogenesis of OA has led the American Academy of Orthopaedic Surgeons (AAOS) to develop recommendations for treatment of knee OA. These include activity modification, weight loss, fitness, range of motion and quadriceps strengthening exercises, patellar tapping, acupuncture, glucosamine, NSAIDS, acetaminophen, analgesics, and injections of intra-articular corticosteroids or hyaluronic acid. Surgical treatments include arthroscopy, meniscectomy, osteotomy and knee replacement surgery. In this context, there is a need for an enhanced method for treating OA in a noninvasive manner.

SUMMARY

In accordance with one or more embodiments and corresponding disclosure thereof, various aspects are described in connection with a method for OA treatment at an affected area or joint. For example, the method may involve identifying a treatment site of the joint, and providing at least one transducer module at the treatment site. The at least one transducer module may be in operative communication with a signal generator module, and may include at least one transducer for delivering stimulative signals, wherein the stimulative signals may include electromagnetic signals and/or ultrasound signals. The method may also involve stimulating (a) bone remodeling, (b) bone cells and associated precursors, and/or (c) pericytes at the joint with the stimulative signals delivered to the treatment site at a user-selected intensity for a user-selected time period by exciting the at least one transducer module with the signal generator module.

In accordance with one or more aspects of the embodiments described herein, there is provided an apparatus for treating OA. For example, the apparatus may include a signal generator for generating stimulative signals (e.g., electromagnetic signals and/or ultrasound signals). The apparatus may include at least one transducer module in operative communication with a signal generator module and configured to be placed at the affected joint. The apparatus may also include a controller interface in operative communication with the signal generator. The apparatus may further include at least one processor in operative communication with the signal generator and the controller interface, wherein the at least one processor may be configured to stimulate bone remodeling at the joint with the stimulative signals delivered to the joint, in response to user input received via the controller interface.

To the accomplishment of the foregoing and related ends, one or more aspects comprise the features hereinafter fully described and particularly pointed out in the claims. The following description and the annexed drawings set forth in detail certain illustrative aspects and are indicative of but a few of the various ways in which the principles of the aspects may be employed. Other novel features will become apparent from the following detailed description when considered in conjunction with the drawings and the disclosed aspects are intended to include all such aspects and their equivalents.

DESCRIPTION

Figure 1:
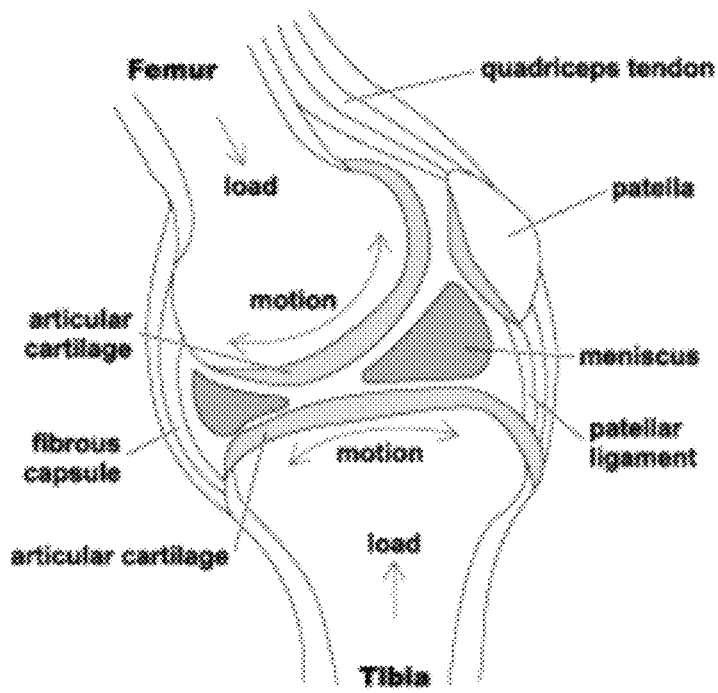
FIG. 1 illustrates a human knee.
Figure 2:
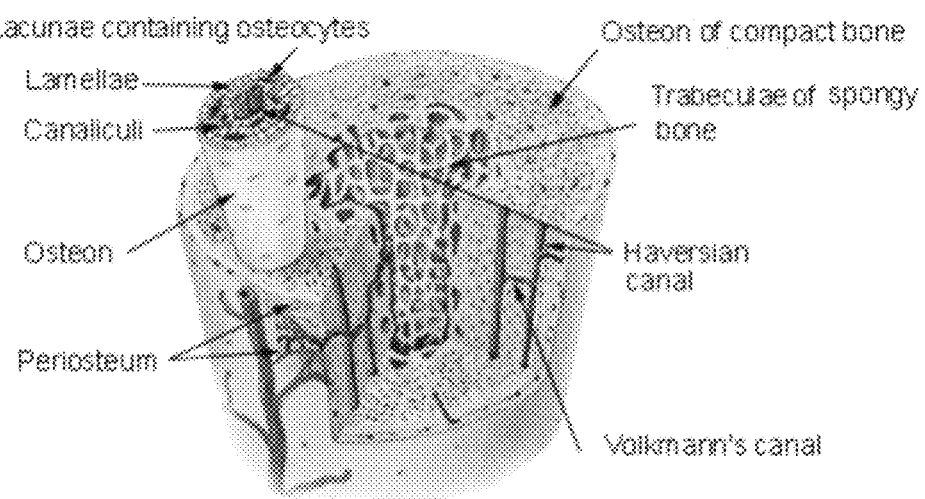
FIG. 2 illustrates cancellous bone and components thereof.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, well-known structures and components are shown in block diagram form in order to avoid obscuring such concepts.

Electric and electromagnetic fields may be generated and applied to bones via currently known techniques, such as, for example, direct current (DC), pulsed electromagnetic fields (PEMFs), combined magnetic fields (CMFs), or capacitive coupling for capacitively coupled electric fields (CCEFs). Physiologic effects of electromagnetic stimulation of bone may include, for example, piezoelectricity, cellular proliferation and/or differentiation, synthesis of extracellular matrix, transmembrane signal transduction, synthesis of growth factors, increased DNA production, altered gene expression, etc. There is also evidence that pericytes may contribute to the ostogenic response to electrical stimulation. Exposure to electromagnetic fields produces a temporal acceleration and quantitative increase in endochondral bone formation and trabecular maturation through the process of bone remodeling.

Another use of electromagnetic stimulation of biologic tissues relates to the stimulation of cartilage cells rather than bone cells. Pulsed electromagnetic fields have been used to stimulate cartilage cells in clinical trials, and capacitively coupled electrical fields have also been shown to stimulate in vivo chondrocytes.

Ultrasound is another technology known to stimulate bone growth and remodeling. Although the mechanism for how ultrasound stimulates bone healing is unknown, it has been hypothesized that the pressure waves it produces provide micro-mechanical stress and strain causing biochemical alterations at the cellular level leading to enhanced bone formation.

In related aspects, since fibrous tissue is nonvascular and normal bone is vascular the bone remodeling associated with electromagnetic stimulation with bone growth stimulators has inherent changes associated with the vascular system. The capillary contained in the growing end of the basic multicellular unit during cancellous bone remodeling is believed by the inventor to redistribute regional blood flow to alleviate subchondral venous congestion and thereby decrease pain with subsequent improvements in the delivery of nutrients that will affect disease progression. It is the commonality of the presence of fibrous tissue in fibrous non-union and in the subchondral cancellous bone in OA, combined with the knowledge that subchondral venous congestion is present in OA and the fact that changes in the anatomic vasculature and circulatory functions are inherent in the process of cancellous bone remodeling, that allow for the OA to be treated via application of the below-described techniques.

In accordance with aspects of the subject of this disclosure, there are provided techniques for the treatment of osteoarthritis (OA) or similar conditions using noninvasive electromagnetic stimulation and/or ultrasound. The use of noninvasive electromagnetic stimulation and/or ultrasound for the treatment of OA is unique from previous treatments of fracture nonunion in that the bone which is present in fracture nonunion is woven bone, whereas with OA the target tissue is cancellous bone. The indication for use is different as well as the target tissue. The current application is unique in that the intended tissue is cancellous bone with alleviation of venous congestion through the process of bone remodeling, as distinct from the target tissue of bone callus as with fracture nonunion.

Figure 3:
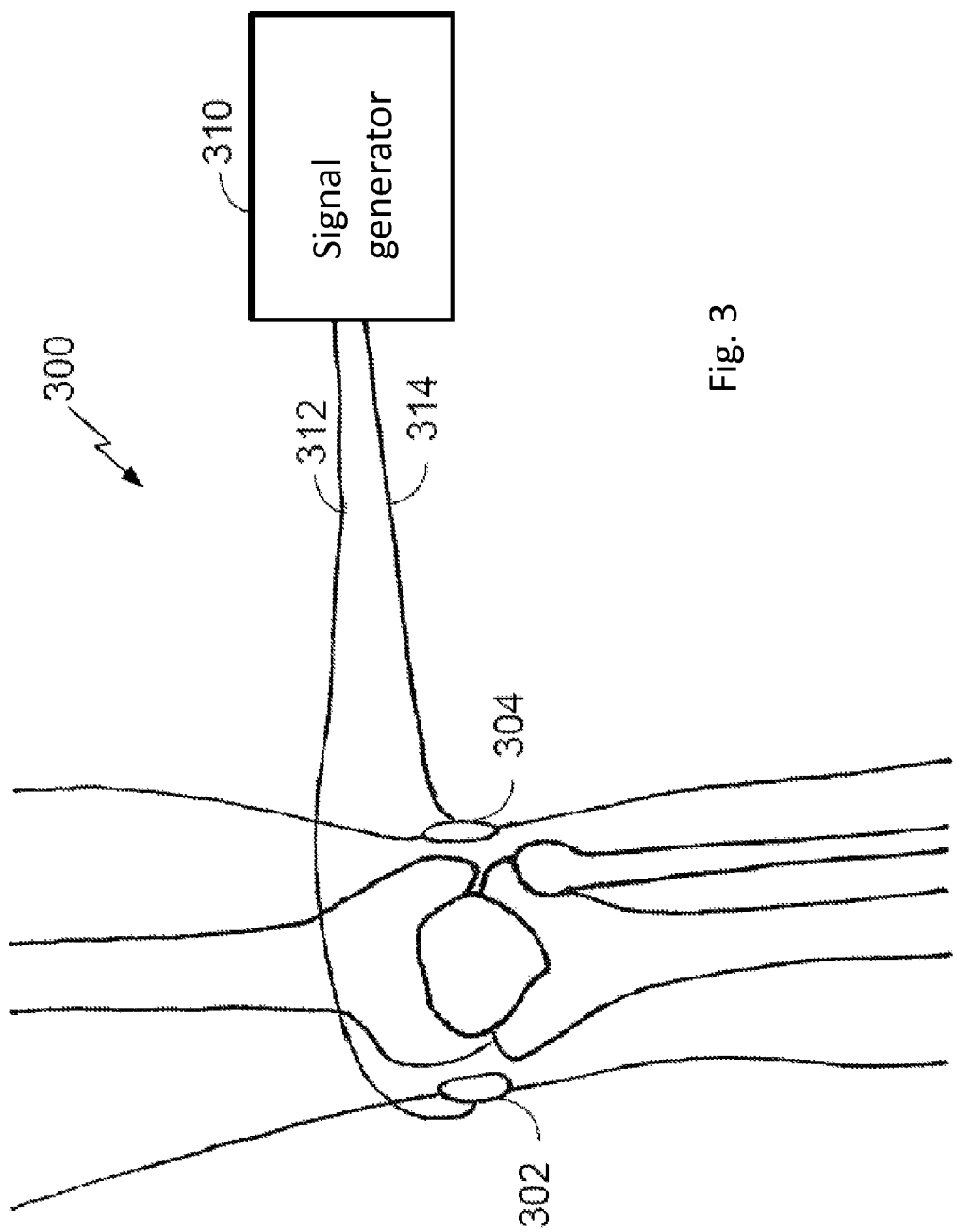
FIG. 3 is a block diagram showing an embodiment of a system for treating a human knee affected by OA.

The technique of application of these electromagnetic and ultrasonic signals to joints affected with OA may be specific for the joint affected and the type of signal. For example, with CCEFs and with ultrasound, electrodes may be placed across the affected joint as is illustrated in FIG. 3, which shows a human knee 300 affected with OA. With continued reference to FIG. 3, electrodes 302 and 304 may be placed on two sides of the knee 300. For example, the electrodes 302 and 304 may be placed on the medial and lateral sides. The electrodes 302 and 304 may be connected to a signal generator 310 via electrical leads 312 and 314, respectively. In one embodiment, the signal generator 310 may comprise a CCEF signal generator and/or an ultrasound generator unit. The signal generator 310 generate stimulative signals (e.g., electromagnetic signals and/or ultrasound signals) delivered to the knee 300 via electrodes 302 and 304. This mode of application has the advantage of ease of use and versatility for use in various joints.

When PEMFs or CMFs are applied there are restrictions of geometry such that it may be desirable to use various frames to support the coils that create these electromagnetic signals. For example, these frames can be circumferential and comprise opposing coils (see FIG. 4) or an open geometry (see FIG. 5). The frame design may be altered for applications to include knees, hips or spine and may be manufactured in various sizes to correlate with the corresponding anatomy. Such frames may encompass the affected joint, may be made in a "C" type shape, or be composed of a single flat coil, allowing the affected joint to be treated by the electromagnetic signals. The signaling parameters and treatment protocols that are used for each of these frames, coils, the geometries and the electrodes may be specific for the signaling modality.

Figure 4:
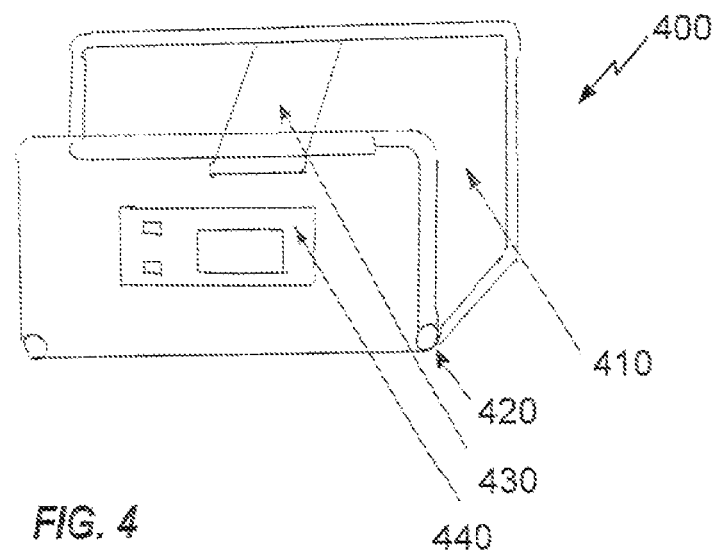
FIG. 4 shows an embodiment of a device for treating OA.

With reference to FIG. 4, there is shown an embodiment of a transducer module 400, which in this example is a frame of circumferential coils. The transducer module 400 may be configured to define an opening 410 for placement of a joint or another affected area. The transducer module 400 may comprise a hinge 420 and/or a latch 430. The transducer module 400 may comprise a patient or user interface 440 for controlling the delivering of stimulative signals to the affected joint/area.

Figure 5:
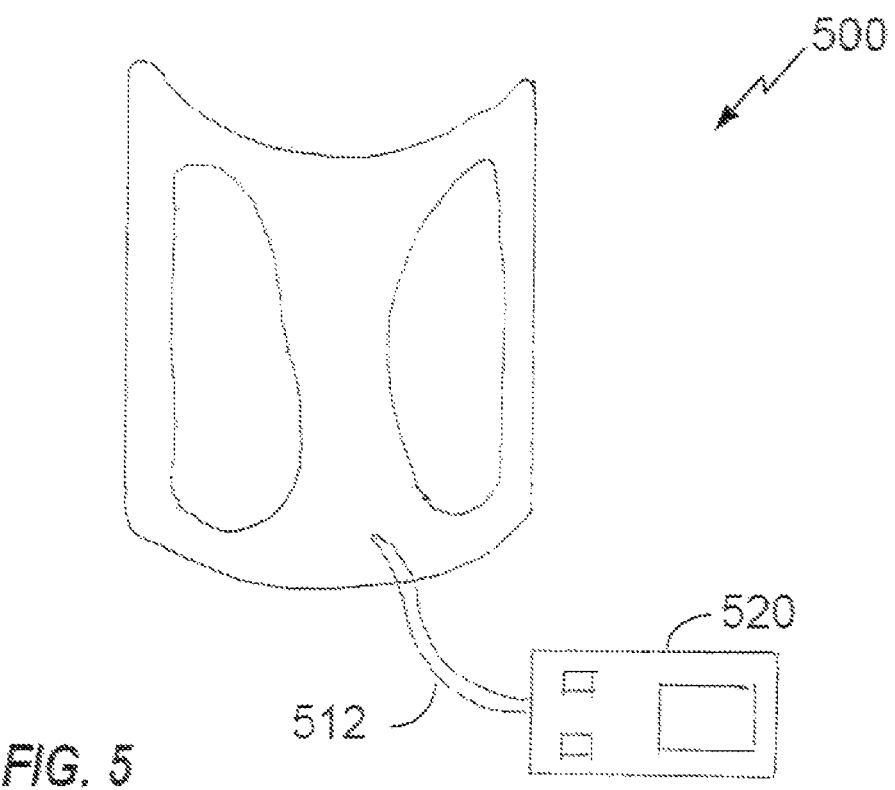
FIG. 5 shows another embodiment of a device for treating OA.

With reference to FIG. 5, there is shown an embodiment of a OA treatment device 500 that comprises a transducer module 500, which in this example is a frame with an open geometry coil. The transducer module 500 may be in operatively coupled to a patient or user interface 520 via a cord or connector 512. The user interface 520 may comprise user input buttons/controllers and display for controlling the characteristics and/or type of the stimulative signals, as well as the manner (e.g., duration, frequency, etc.) in which the stimulative signals are delivered to a treatment site of the affected area.

When ultrasound is used, the method of application may begin with a medical diagnosis of OA of a joint in a human. The ultrasonic signaling may be applied across an affected OA joint through electrode patches placed on the skin overlying the joint. For example, a treatment regimen with low intensity pulsed ultrasound may be about twenty minutes per day for a period of several months, using dual frequency treatment heads of about 1 MHz and 3 MHz, with a maximum intensity of about 400 milliwatts and low beam nonuniformity ratio of about 3.1 to about 3.5.

In related aspects, a variety of other ultrasonic signaling parameters and geometries may be used. For example, a single transducer rather than two electrodes could be used where an ultrasound transducer in contact with the skin of the patient transmits ultrasound pulses to the affected joint. In one approach, alternate signaling characteristics may include a nominal frequency of the ultrasound of about 1.5 MHz, the width of each pulse varied between about 10 and about 2,000 microseconds, and the pulse repetition rate varied between about 100 and about 1,000 Hz. For example, the power level of the ultrasound may be maintained below about 100 milliwatts per square centimeter. Treatment duration may be no more than about twenty minutes per day for a period of several months. It is noted that variety of other applicable signal characteristics and geometries may be implemented for ultrasound stimulation of bone cells or the bone remodeling process as described herein.

In one approach, electromagnetic signaling from CCEFs small skin pads/electrodes may be placed on either side of the affected joint and worn for about 24 hours per day until healing occurs, or up to 9 months or other time period appropriate for a given condition being treated for a specific patient. For example, electrodes may be applied across a human joint with a medical diagnosis of OA with the electrodes at about 180 degrees from each other in the transverse plane with a tolerance of misalignment of plus or minus about 20 degrees. Electrodes are preferably placed in an orientation to minimize effects of flexion and extension of the affected joint on the positioning and adherence of the electrodes. For example with use in the knee, the electrodes may be placed on the lateral aspects of the knee. In the plane of the long axis of the bones proximal and distal to the joint, the tolerance of misalignment may be equal to the diameter of an electrode, typically about 1⅜ inch. These considerations of electrode placement and care, as well as tolerances, are also applicable to the treatment with ultrasound which similarly utilizes electrodes.

In related aspects, it is advisable to remove the hair at the electrode site. The signal generator and connecting cables may be removed before showering. Protective covers may be used to prevent the need to remove the adhesive electrodes during periods of personal hygiene. The essential signal characteristics may be between about 5 milliamps and about 10 milliamps. The voltage which is the driving force for the delivery of the current may be less critical and typically between about 3.0 V and about 6.3 V. For example, the signal generator may be worn on a belt with cables connecting the signal generator to the electrodes.

Pulsed electromagnetic fields are may be delivered via treatment coils placed adjacent to the affected joint, and may be used, for example, for up to about 6-8 hours per day for about 3 to 6 months. Combined magnetic fields deliver a time-varying magnetic field by superimposing the time-varying magnetic field onto an additional static magnetic field. A variety of signal parameters may be used for this purpose and electromagnetic frequencies in a range of about 0 to about 150 hertz may be used to stimulate bone cells, and thereby stimulate bone remodeling. It is noted that a variety of other known signal characteristics may be applied using PEMFs and CMF's to generate electromagnetic signals known to stimulate bone remodeling, bone cells and precursors, and/or pericytes.

In accordance with one or more aspects of the embodiments described herein, the method of application may begin with a medical diagnosis of OA of a joint in a human. The affected joint may be then placed within the device which creates the electromagnetic signal. When this device uses the geometry of a circumferential frame, as shown in the embodiment of FIG. 4, the latch may be opened and the affected joint may be centered in the device and closed. When the geometry used is on an open frame, as shown in the embodiment of FIG. 5, the affected joint may be centered with the use of adjoining straps or the like. The device may be activated with the use a patient interface or the like such that the electromagnetic field is applied.

In related aspects, when CMF's are used, the treatment period may be about 30 minutes daily with a duration of up to about 9 months or other defined time period, depending on the particular patient and nature of the OA. In further related aspects, the device power source may be a battery or other energy cell. Manufacturing components may place restrictions on the storage temperature of the device to be between about 5 and about 140 degrees Fahrenheit, with an operating temperature range between about 50 degrees and about 100 degrees Fahrenheit, and an operating humidity range maximum of about 85% Relative Humidity.

It is noted that the discussion of PEMFs or CMF's for the treatment of OA of the knee is for illustrative purposes as a preferred embodiment of the design; however, other devices such as, for example, capacitively coupled electrical fields, direct electrical stimulation, direct ultrasound, or the like, may also be implemented. The example of treatment of OA of the knee is not intended to limit the scope or spirit of the techniques described herein. Rather, OA of other areas of the body (e.g., hip, vertebra, etc.) may also benefit from the techniques described herein, with the design of the frame or electrode geometries being configured for the pertinent treatment site/anatomy.

In view of exemplary systems shown and described herein, methodologies that may be implemented in accordance with the disclosed subject matter, will be better appreciated with reference to various flow charts. While, for purposes of simplicity of explanation, methodologies are shown and described as a series of acts/blocks, it is to be understood and appreciated that the claimed subject matter is not limited by the number or order of blocks, as some blocks may occur in different orders and/or at substantially the same time with other blocks from what is depicted and described herein. Moreover, not all illustrated blocks may be required to implement methodologies described herein.

Figure 6:
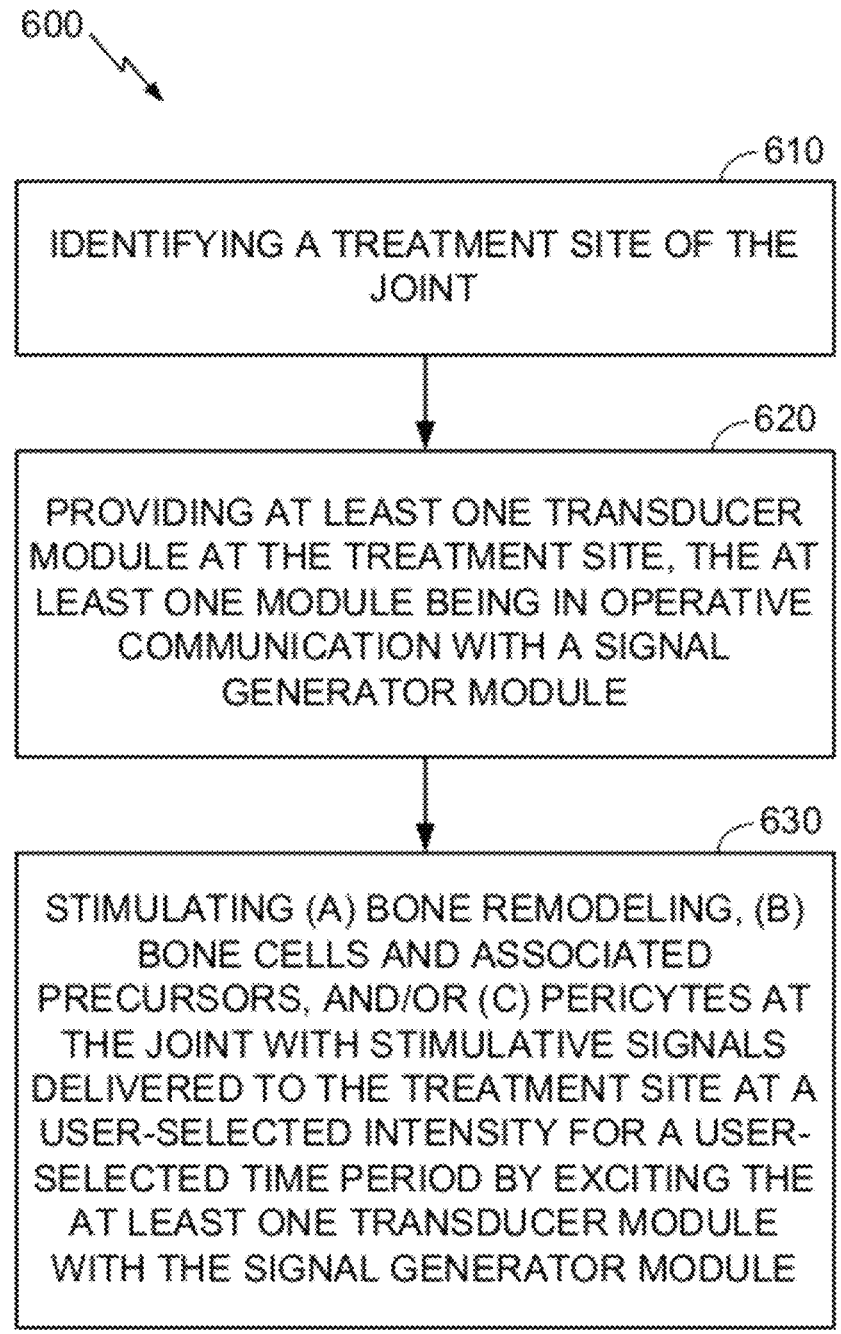
FIG. 6 illustrates an embodiment of a methodology for treating OA of an affected area/joint.

In accordance with one or more aspects of the subject of this disclosure, there are provided methods for treating OA of an affected area or joint (e.g., knee, hip, and vertebra). With reference to FIG. 6, illustrated is a methodology 600 that may involve, at 610, identifying a treatment site of the joint. The method 600 may involve, at 620, providing at least one transducer module at the treatment site, the at least one transducer module being in operative communication with a signal generator module. The at least one transducer module may include at least one transducer for delivering stimulative signals, the stimulative signals comprising electromagnetic signals and/or ultrasound signals. The method 600 may involve, at 630, stimulating (a) bone remodeling, (b) bone cells and associated precursors, and/or (c) pericytes at the joint with the stimulative signals delivered to the treatment site at a user-selected intensity for a user-selected time period by exciting the at least one transducer module with the signal generator module, thereby treating the OA. It is noted that the stimulative signals stimulate bone cells and the remodeling process of the bone cells, with the subchondral bone and hyaline cartilage as a functional unit. It is also noted that the at least one transducer module may include frame(s) and/or coil(s), each comprising a geometry corresponding to an anatomical characteristic of the joint or treatment area.

Figure 7:
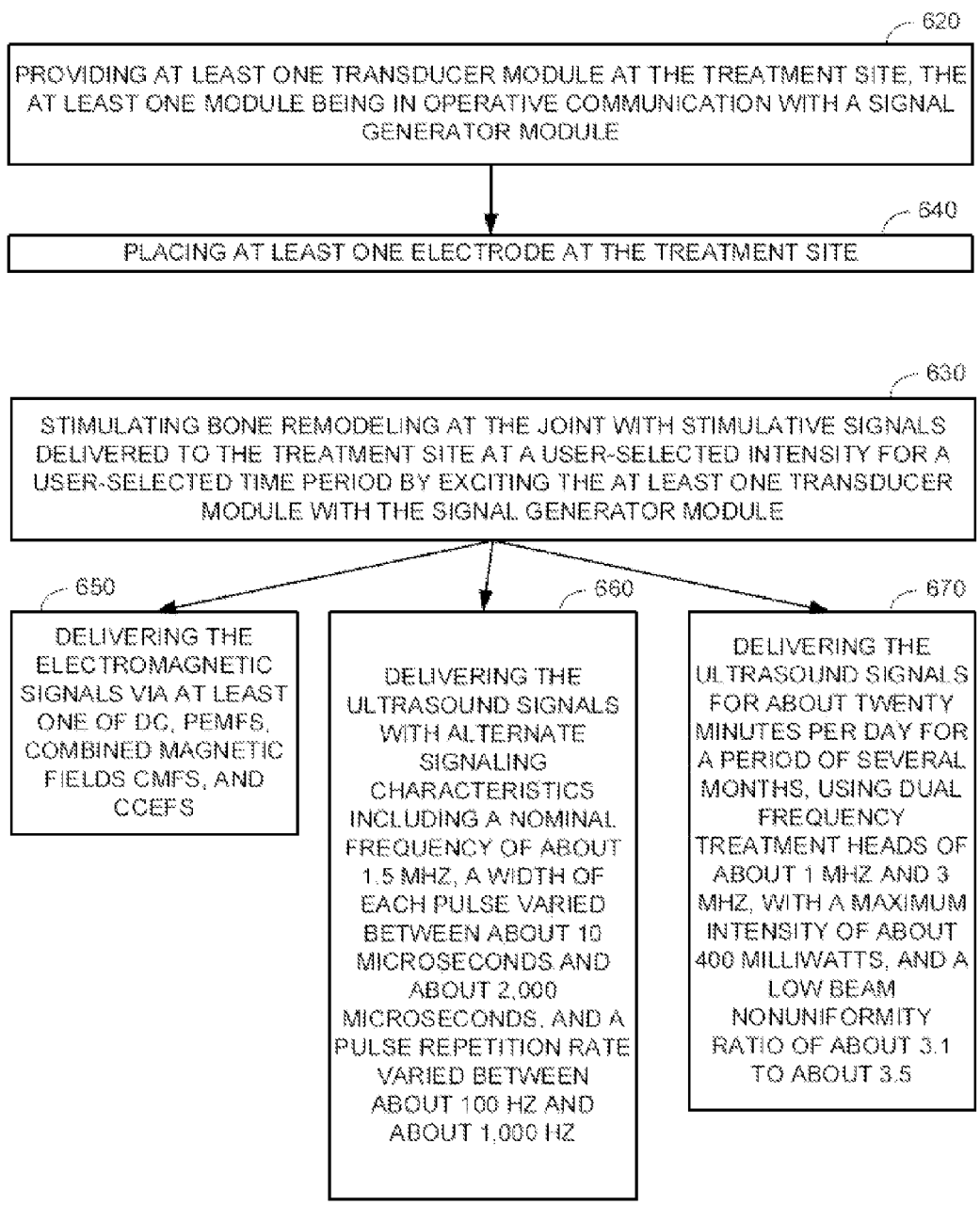
FIG. 7 shows further aspects of the methodology of FIG. 6.

With reference to FIG. 7, providing the at least one transducer module may involve, at 640, placing at least one electrode at the treatment site. Stimulating (a) the bone remodeling, (b) the bone cells and the associated precursors, and/or (c) the pericytes may involve, at 650, delivering the electromagnetic signals via at least one of DC, PEMFs, combined magnetic fields CMFs, and CC. For example, the user-selected intensity of the electromagnetic signals include: (a) a current of about 5 milliamps and about 10 milliamps; and/or (b) a driving force voltage of about 3.0 V and about 6.3 V. In related aspects, the user-selected time period may be about 6 hours to about 8 hours per day, for about 3 to about 9 months.

In the alternative, or in addition, Stimulating (a) the bone remodeling, (b) the bone cells and the associated precursors, and/or (c) the pericytes may involve, at 660, delivering the ultrasound signals with alternate signaling characteristics including a nominal frequency of about 1.5 MHz, a width of each pulse varied between about 10 microseconds and about 2,000 microseconds, and a pulse repetition rate varied between about 100 Hz and about 1,000 Hz. In another embodiment, Stimulating the (a) bone remodeling, (b) the bone cells and the associated precursors, and/or (c) the pericytes may involve may involve, at 670, delivering the ultrasound signals for about twenty minutes per day for a period of several months, using dual frequency treatment heads of about 1 MHz and 3 MHz, with a maximum intensity of about 400 milliwatts, and a low beam nonuniformity ratio of about 3.1 to about 3.5.

Figure 8:
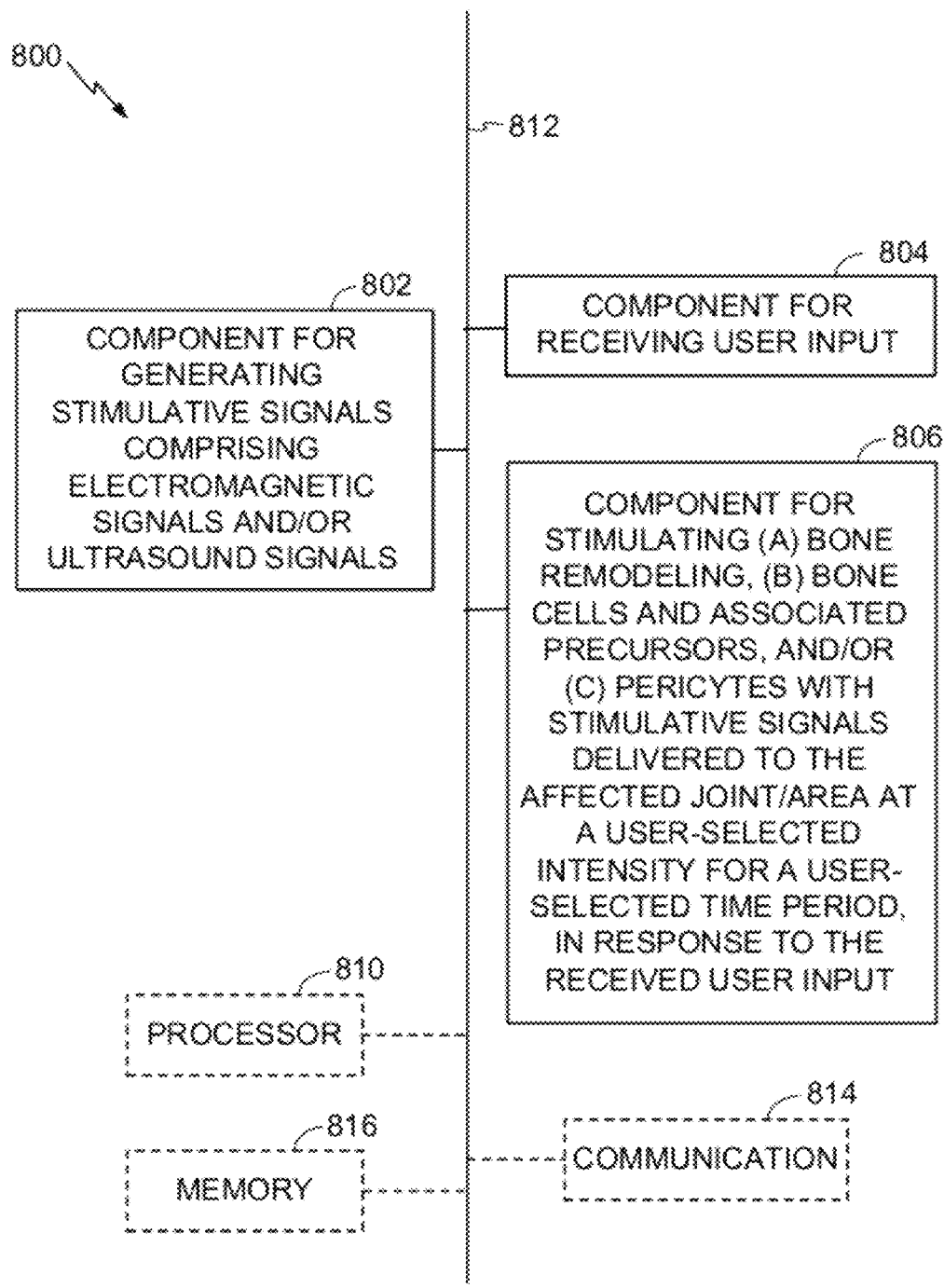
FIG. 8 illustrates an embodiment of an apparatus for OA treatment, in accordance with the methodologies of FIGS. 6-7.

In accordance with one or more aspects of the embodiments described herein, there are provided devices and apparatuses for treating OA of an affected joint/area, as described above with reference to FIGS. 6-7. With reference to FIG. 8, there is provided an exemplary apparatus 800 that may be configured as a patient treatment device/system, or as a processor or similar component for use within the device/system. The apparatus 800 may include functional blocks that can represent functions implemented by a processor, software, or combination thereof. As illustrated, in one embodiment, the apparatus 800 may comprise an electrical component or module 802 for generating stimulative signals comprising electromagnetic signals and/or ultrasound signals. The apparatus 800 may comprise an electrical component 804 for receiving user input. The apparatus 800 may comprise an electrical component 806 for stimulating (a) bone remodeling, (b) bone cells and associated precursors, and/or (c) pericytes with stimulative signals delivered to the affected joint/area at a user-selected intensity for a user-selected time period, in response to the received user input.

In related aspects, the apparatus 800 may optionally include a processor component 810 having at least one processor, in the case of the apparatus 800 configured as a network entity, rather than as a processor. The processor 810, in such case, may be in operative communication with the components 802-806 via a bus 812 or similar communication coupling. The processor 810 may effect initiation and scheduling of the processes or functions performed by electrical components 802-806.

In further related aspects, the apparatus 800 may include a communication/transceiver component 814. The apparatus 800 may optionally include a component for storing information, such as, for example, a memory device/component 816. The computer readable medium or the memory component 816 may be operatively coupled to the other components of the apparatus 800 via the bus 812 or the like. The memory component 816 may be adapted to store computer readable instructions and data for effecting the processes and behavior of the components 802-806, and subcomponents thereof, or the processor 810, or the methods disclosed herein. The memory component 816 may retain instructions for executing functions associated with the components 802-806. While shown as being external to the memory 816, it is to be understood that the components 802-806 can exist within the memory 816.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. A noninvasive method for treating osteoarthritis (OA) of an OA affected joint at the site of a junction between bones, comprising:
   identifying a treatment site of the OA affected joint;
   providing at least one transducer module at the treatment site, the at least one transducer module being in operative communication with a signal generator module and comprising at least one transducer for delivering stimulative signals, the stimulative signals comprising at least ultrasound signals with a maximum intensity of about 100 milliwatts/cm$^2$;
   stimulating bone remodeling at the joint with the stimulative signals delivered to the treatment site at a user-selected intensity for a user-selected time period by exciting the at least one transducer module with the signal generator module;
   repeating the providing and stimulating over time consistent with a treatment protocol; and
   alleviating, in response to the repeating, OA conditions at the OA affected joint;
   wherein the alleviating comprises alleviating venous congestion of cancellous bone at the affected joint.

2. The method of claim 1, wherein the affected joint comprises one of a knee, hip, and vertebra.

3. The method of claim 1, wherein providing the at least one transducer module comprises placing at least one electrode at the treatment site.

4. The method of claim 1, wherein the stimulative signals further comprise at least electromagnetic signals, and wherein stimulating the bone remodeling comprises delivering the electromagnetic signals via at least one of direct current (DC), pulsed electromagnetic fields (PEMFs), combined magnetic fields (CMFs), and capacitively coupled electric fields (CCEFs).

5. The method of claim 4, wherein the user-selected intensity of the electromagnetic signals comprises: (a) a current of between about 5 milliamps and about 10 milliamps; and (b) a driving force voltage of between about 3.0 V and about 6.3 V.

6. The method of claim 4, wherein the electromagnetic signals comprises frequencies in the range of about 0 to about 150 hertz, and wherein the user-selected time period comprises about 6 hours to about 8 hours per day, for about 3 to about 9 months.

7. The method of claim 1, wherein stimulating the bone remodeling comprises delivering the ultrasound signals with alternate signaling characteristics including a nominal frequency of about 1.5 MHz, a width of each pulse varied between about 10 microseconds and about 2,000 microseconds, and a pulse repetition rate varied between about 100 Hz and about 1,000 Hz.

8. The method of claim 1, wherein stimulating the bone remodeling comprises delivering the ultrasound signals for about twenty minutes per day for a defined period, using dual frequency treatment heads of about 1 MHz and 3 MHz, and a low beam nonuniformity ratio of about 3.1 to about 3.5.

9. A noninvasive method for treating osteoarthritis (OA) of an affected joint, comprising:
   identifying a treatment site of the joint;
   providing at least one transducer module at the treatment site, the at least one transducer module being in operative communication with a signal generator module and comprising at least one transducer for delivering a combination of electromagnetic signals and ultrasound signals, the ultrasound signals having a maximum intensity of about 100 milliwatts/cm$^2$;
   stimulating bone remodeling at the joint with the electromagnetic signals and the ultrasound signals delivered to the treatment site by exciting the at least one transducer module with the signal generator module;
   repeating the providing and stimulating over time consistent with a treatment protocol; and
   alleviating, in response to the repeating, OA conditions at the OA affected joint;
   wherein the alleviating comprises alleviating venous congestion of cancellous bone at the affected joint.

10. The method of claim 9, wherein stimulating the bone remodeling comprises delivering the electromagnetic signals via at least one of direct current (DC), pulsed electromagnetic fields (PEMFs), combined magnetic fields (CMFs), and capacitively coupled electric fields (CCEFs).

11. The method of claim 10, the electromagnetic signals comprise: (a) a current of between about 5 milliamps and between about 10 milliamps; and (b) a driving force voltage of about 3.0 V and about 6.3 V.

12. The method of claim 9, wherein stimulating the bone remodeling comprises delivering the ultrasound signals with alternate signaling characteristics including a nominal frequency of about 1.5 MHz, a width of each pulse varied between about 10 microseconds and about 2,000 microseconds, and a pulse repetition rate varied between about 100 Hz and about 1,000 Hz.

13. A noninvasive method for treating osteoarthritis (OA) of an affected joint, comprising:
   identifying a treatment site of the joint;
   providing at least one transducer module at the treatment site, the at least one transducer module being in operative communication with a signal generator module and comprising at least one transducer for delivering stimulative signals, the stimulative signals comprising at least ultrasound signals having a maximum intensity of about 100 milliwatts/cm$^2$;
   stimulating at least one of (a) bone cells and associated precursors and (b) pericytes at the joint with the stimulative signals delivered to the treatment site at a user-selected intensity for a user-selected time period by exciting the at least one transducer module with the signal generator module;
   repeating the providing and stimulating over time consistent with a treatment protocol; and
   alleviating, in response to the repeating, OA conditions at the OA affected joint
   wherein the alleviating comprises alleviating venous congestion of cancellous bone at the affected joint.

14. The method of claim 13, wherein stimulating the at least one of (a) the bone cells and the associated precursors and (b) the pericytes comprises additionally delivering electromagnetic signals via at least one of direct current (DC), pulsed electromagnetic fields (PEMFs), combined magnetic fields (CMFs), and capacitively coupled electric fields (CCEFs).

15. The apparatus of claim 13, wherein stimulating comprises delivering the ultrasound signals with alternate signaling characteristics including a nominal frequency of about 1.5 MHz, a width of each pulse varied between about 10 microseconds and about 2,000 microseconds, and a pulse repetition rate varied between about 100 Hz and about 1,000 Hz.

16. The method of claim 13, wherein stimulating comprises delivering the ultrasound signals for about twenty minutes per day for a defined period, using dual frequency treatment heads of about 1 MHz and 3 MHz, and a low beam nonuniformity ratio of about 3.1 to about 3.5.

* * * * *